United States Patent [19]

Deutsch et al.

[11] Patent Number: 4,957,728

[45] Date of Patent: Sep. 18, 1990

[54] KIT FOR PREPARING TC (III)-99M MYOCARDIAL IMAGING AGENTS THAT ARE EFFECTIVE IN HUMANS

[75] Inventors: Edward A. Deutsch; Karen F. Libson, both of Cincinnati, Ohio

[73] Assignee: University of Cincinnati, Cincinnati, Ohio

[21] Appl. No.: 463,403

[22] Filed: Jan. 11, 1990

Related U.S. Application Data

[62] Division of Ser. No. 354,491, May 19, 1989, Pat. No. 4,917,879.

[51] Int. Cl.$^5$ .................... A61K 49/02; B65D 69/00
[52] U.S. Cl. ........................................ 424/1.1; 534/14; 206/569
[58] Field of Search ................ 424/1.1, 9; 534/14, 534/10; 252/1; 206/569

[56] References Cited

U.S. PATENT DOCUMENTS 4,795,626  1/1989  Deutsch et al. ............... 424/1.1
4,917,879  4/1990  Deutsch et al. ............... 424/1.1

Primary Examiner—John B. Maples
Attorney, Agent, or Firm—Wood, Herron & Evans

[57] ABSTRACT

A myocardial imaging agent for humans is a technetium(III) complex ligated in the planar positions by a tetradentate ligand such as (acac)$_2$en and in the axial positions by an ether containing phosphine ligand such as tris(3-methoxy-1-propyl)-phosphine. The agent exhibits extremely rapid blood clearance after injection into a human and has a sufficiently high heart/liver and heart/lung ratios to provide effecitve myocardial images.

4 Claims, 1 Drawing Sheet

BLOOD CLEARANCE/STRESS

BLOOD CLEARANCE/REST

KIT FOR PREPARING TC (III)-99M MYOCARDIAL IMAGING AGENTS THAT ARE EFFECTIVE IN HUMANS

This is a division of application Ser. No. 354,491, filed May 19, 1989, now U.S. Pat. No. 4,917,879.

BACKGROUND OF THE INVENTION

Several non-invasive methods of imaging body organs have been developed over the past decades. These procedures are based on the tendency of a body organ to concentrate some detectable chemical. Particularly useful chemicals are those which emit gamma radiation. Subsequent scanning of the organ with a gamma ray camera provides an image of the organ from which diagnostic information can be obtained. $^{99m}$Tc (Tc-99m) has been found to be particularly useful in this area because of its half-life and gamma ray emission.

Over the past several years different Tc-99m compounds have been disclosed for use as positive myocardial imaging agents. These different imaging agents, based on substantially different chemistries, have exhibited varying levels of utility in different mammals. To effectively image the heart the agent must localize in the heart and at the same time rapidly clear from neighboring organs such as the lungs and in particular the liver. Further, the imaging agent must not bind tightly to the blood or else image quality will be poor. An imaging agent which localizes in the heart and at the same time localizes in the liver does not provide a good image of the heart since the apex of the human heart is often obscured by the liver.

One recent patent which discloses Tc-99m myocardial imaging agents is Deutsch et al U.S. Pat. No. 4,795,626. This discloses a type of myocardial imaging agent which due to its ligand system is not reducible in vivo. Thus, the disclosed Tc(III) complexes remain in this oxidation state for imaging purposes. This has been found somewhat useful in myocardial imaging.

Unfortunately, the prototypical agent of this class has relatively slow blood clearance and high liver uptake which gives rise to rather low heart/liver ratio. This is reported in the *Journal of Nuclear Medicine*, 28 1070 1000, 1987. The ligand system acac$_2$en bonded to the four planar coordinations sites of the technetium and PMe$_3$ (trimethylphosphine) bonded to the axial sites simply did not provide an efficacious myocardial imaging agent in humans.

One commercially acceptable product is Cardiolite sold by DuPont. This is an isonitrile Tc(I) complex. The isonitrile ligands contain alkyl ether groups. Also, *Nuclear Medicine Communication*, 10(4), Apr., 1989, p.245 reports myocardial imaging agents in which $^{99m}$Tc is complexed to bidentate phosphorus ligands containing alkyl ether groups. This brief abstract reports a heart/liver ratio of 0.75 which is lower than what is required to obtain a good myocardial image.

SUMMARY OF THE INVENTION

The present invention is premised on the realization that Tc(III) myocardial imaging agents which are not reducible in vivo can be very effective myocardial imaging agents if the ligands contain one or more ether moieties in the ligand system.

More particularly, the present invention is premised on the realization that an effective myocardial imaging agent for humans can be prepared by ligating a tetradentate ligand system to the 4 planar coordination bonding sites of an octahedrally coordinated technetium center and bonding ligands containing ether moieties to the axial positions of the technetium center. Specifically, the present invention is premised on the realization that a Tc(III) acac$_2$en complex having alkyl ether substituted phosphine ligands at the axial positions provides a commercially viable heart imaging agent.

The present invention will be further appreciated in light of the following detailed description and drawing in which:

DETAILED DESCRIPTION OF THE INVENTION

Figure 1:
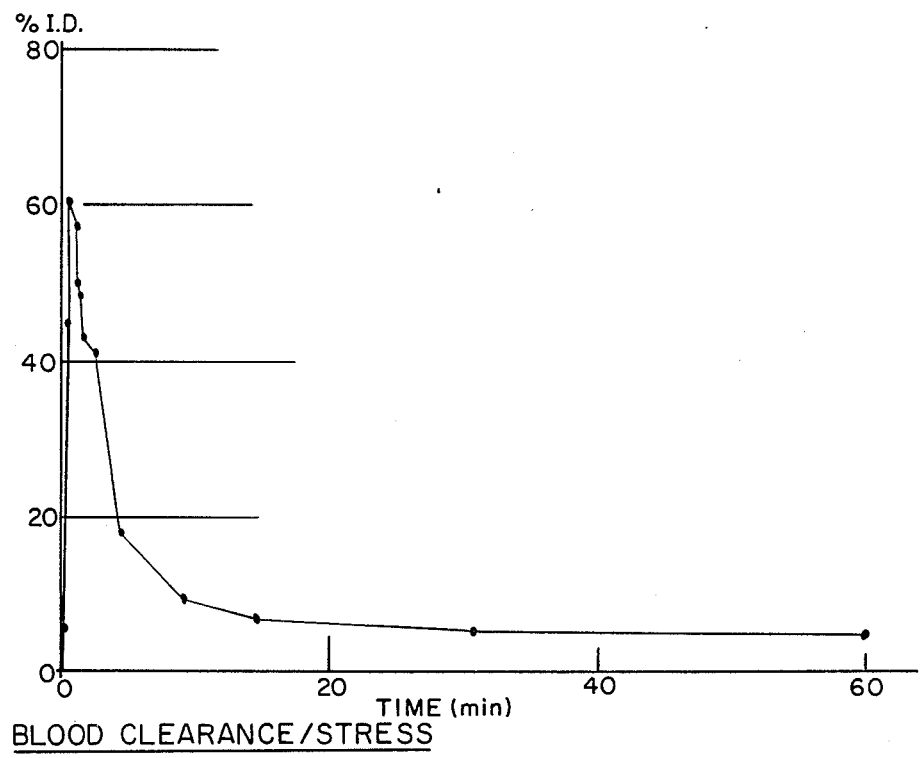
FIG. 1 is a graph showing blood clearance from a human volunteer during a stress evaluation of a myocardial imaging agent made according to the present invention.

The technetium compounds which are useful as myocardial imaging agents in humans are hexadentate technetium complexes which have an overall cationic charge. More specifically, the complexes will be technetium complexes in the +3 oxidation state coordinatively bonded to six atoms as shown in Formula 1.

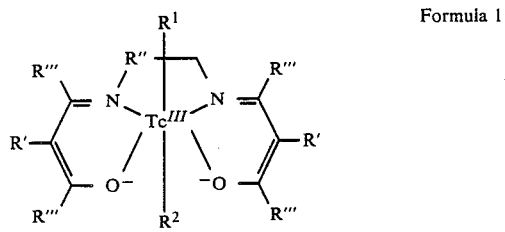

Formula 1

$R'$ and $R'''$ represent H, hydroxyl, $C_1$-$C_5$ alkyl, $C_1$-$C_5$ alkyl substituted by hydroxyl, ether, amide, ketone, aldehyde or nitrile group.

$R''$ represents $C_1$-$C_4$ alkylene, $C_1$-$C_4$ alkenyl which may be substituted with hydroxyl, ether, amide, ester, ketone, aldehyde or nitrile group.

The present technetium compound is bonded generally to three ligands, two axial ligands $R_1$ and $R_2$ as in Formula 1 and a tetradentate ligand having the following formula:

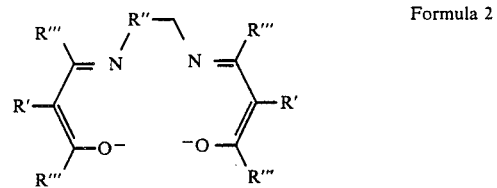

Formula 2

The preferred tetradentate ligand is N,N'-ethylenebis(acetylacetone iminato) hereinafter referred to as (acac)$_2$en wherein $R''$ represents methylene and all the R's represent hydrogen and all the R'''s represent methyl. Also suitable tetradentate ligands include N,N'-ethylenebis(tertbutylacetoacetate iminato) hereinafter referred to as (buac)$_2$en, N,N'-ethylenebis(benzoylacetone iminato) also referred to as (bzac)$_2$en, N,N'- ethylenebis(3-bromoacetyacetone iminato) also referred to as (brac)₂en and N,N'-methylethylenebis(acetylacetone iminato) also referred to as (acac)₂pn.

Ligands $R_1$ and $R_2$ also referred to as the axial ligands represent the same or different ligands both falling within the following general formula:

Formula 3 wherein $R_3$ and $R_4$ represent a moiety having the following general formulas 4 and 5:

Formula 4

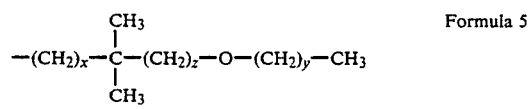
Formula 5

$X = 1-4$
$Y = 0-4$
$Z = 0-4$ and wherein $R_5$ can represent the same moieties represented by $R_3$ and $R_4$ above or may in addition represent —OCH₃, and $C_1-C_4$ alkyl. Such a ligand can be made according to the following example.

EXAMPLE 1

Standard procedures are used to convert 22.5 grams of 3-methoxy-1-propylchloride (CH₃OCH₂CH₂CH₂Cl) and 4.9 g Mg metal to the corresponding Grignard reagent in 110 mL tetrahydrofuran. To the Grignard reagent cooled in a dry ice acetone bath is slowly added 4.6 g of phosphorus trichloride in 40 mL of tetrahydrofuran. The reaction mixture is then allowed to warm to room temperature, and is subsequently heated at reflux for 30 min. This reaction mixture is then cooled to 10° C., and 70 mL of a saturated aqueous solution of ammonium chloride is added. This hydrolyzed mixture is then filtered, and the aqueous layer is removed. The organic layer is dried over potassium carbonate and magnesium sulfate, the tetrahydrofuran is removed by distillation, and the desired phosphine product (P(CH₂CH₂CH₂OCH₃)₃=TMPP) is recovered by vacuum distillation (114–116° C. at 1.5 mm Hg). This phosphine is converted to the hydrochloride adduct (P(CH₂CH₂CH₂OCH₃)₃+HCl=TMPP.HCl) with gaseous HCl (yield=5.8 g, 70%). 31-P NMR shows a single peak at −29.844 ppm (vs. H3P04) for the free phosphine, and a doublet at 20.654, 16.406 ppm (vs. H₃PO₄) for the hydrochloride adduct. FAB-MS (positive ion mode) shows a parent peak at 251 amu for the hydrochloride adduct.

The ligated technetium complex shown in Formula 1 is manufactured in a two step process. A 99m-pertechnetate solution is obtained from a 99-Mo generator. This method of obtaining $^{99m}Tc$ is well known to those skilled in the art and is disclosed for example in Deutsch et al U S. Pat. No. 4,489,054 incorporated herein by reference. This is also disclosed in Glavan et al U.S. Pat. No. 4,374,821 also incorporated herein by reference. This pertechnetate can be diluted to the desired radioactive concentration of 10–100 mCi/mL with normal saline.

The $^{99m}TcO_4^-$ (pertechnetare) in which Tc has an oxidation state of +7 is reduced to a technetium +5 complex having a formula $^{99m}Tc^VO(L)^+$. This is formed by heating $^{99m}TcO_4^-$ in the presence of the tetradentate ligand and a reducing agent such as stannous chloride or sodium borohydride. In the second step the $^{99m}Tc^VOL^+$ complex is further reduced by treating it with the axial ligand of Formula 3 at slightly elevated temperatures, i.e., heating the $^{99m}Tc(V)$ complex in the presence of the ligand. A chemical reducing agent such as borohydride salts, stannous ion salts or hyposulfite salts can also be added.

The preparation of the Tc(V) complex is further described in Examples 2 and 3 wherein the ligand is (acac)₂en.

EXAMPLE 2

Preparation of $^{99m}Tc^VO(acac)_2en^+$ in Ethanol

Pertechnetate is purified according to the method disclosed in U.S. Pat. No. 4,778,672. A C18 sep-pak cartridge was rinsed with 5 mL ethanol and then 3 mL of 0.01 M tetrabutylammonium bromide in water. A desired amount of $^{99m}TcO_4^-$ in saline was combined with 1 mL of 0.1 M tetrabutylammonium bromide, mixed well, and passed slowly through the C18 Sep-pak. The Sep-pak was washed with 10 mL water, 10 mL air were passed through, and the activity eluted with 1–2 mL ethanol.

A solution of 17 mg H₂acac₂en in 0.25 mL is combined with 1 mL of the above tetrabutylammonium 99m-pertechnetate solution and the resulting solution is deaereated for 15 minutes. Then 20 microliters of 1 M KOH and 10 microliters of a freshly prepared solution of 30 mg SnCl₂ in 20 mL ethanol are added. The mixture is incubated at 90° C. for 15 minutes.

EXAMPLE 3

Preparation of $^{99m}TcO_2$ (acac)₂en⁺ in Water 17 mg of H₂acac₂en was dissolved in 0.1 mL of ethanol. Then 0.1 mL of $^{99m}TcO_4^-$ and 0.9 mL of water was added and the mixture deareated for 15 minutes with scrubbed argon. 20 microliters of 1 M KOH and the reducing agent were added next. The best results were obtained with 2–20 microliters of a solution of 0.1 mmole (19mg) stannous chloride in 20 mL H₂O.

The mixture was heated for 15 minutes at 90° C. and cooled to room temperature. The reaction was monitored by HPLC on a PRP-1 column in 90% MeOH/0.01 M Na phosphate and 0.01 M Na heptanesulfonate (pH 7.0) at a flow rate of 1 mL/min. The Tc(V)O(acac₂en)⁺ cation elutes at 4.0–4.2 min. (As in all cases the positive charge of the cation is offset by a biologically acceptable anion such as chloride, as is well known.)

According to the present invention a myocardial imaging agent is prepared by reducing the $^{99m}Tc(V)$ complex as prepared in Examples 2 and 3 to a $^{99m}Tc(III)$ complex. To accomplish this, the $^{99m}Tc(V)$ complex is combined with an ether substituted phosphine ligand such as P(CH₂CH₂CH₂OCH₃)₃. A solution of the ligand is introduced, at ambient or elevated temperature. This acts to reduce the $^{99m}Tc(V)$ complex to a $^{99m}Tc(III)$ complex. The $^{99m}Tc(III)$ complex can then be purified on cationic exchange resin or a reversed phase C₁₈ Sep-Pak. The 99mTc(III) complex will have the structure of Formula 1.

This is further described in Examples 4 and 5.

EXAMPLE 4

0.3 mL of 0.1 M aqueous TMPP.HCl solution from Example 1 is added to the $^{99m}$Tc(V) preparation from Example 2 and the mixture incubated for 15 minutes at 70° C.

The preparation is diluted with 20 mL deareated water (filtering may be needed to remove precipitated ligand) and loaded on a C18 Sep-pak which was prewashed with 5 mL ETOH and 20 mL H$_2$O. The cartridge is rinsed with 20 mL H$_2$O and then twice with 2 mL 80% ethanol-water. The compound is eluted in 1–2 mL 80% ethanol-saline.

EXAMPLE 5

0.3 mL of a 0.1 M TMPP.HCl solution from Example 1 was added to the $^{99m}$Tc(V) preparation from Example 3 and incubated at 70° C. for 15 minutes. This is then ready for use.

Figure 2:
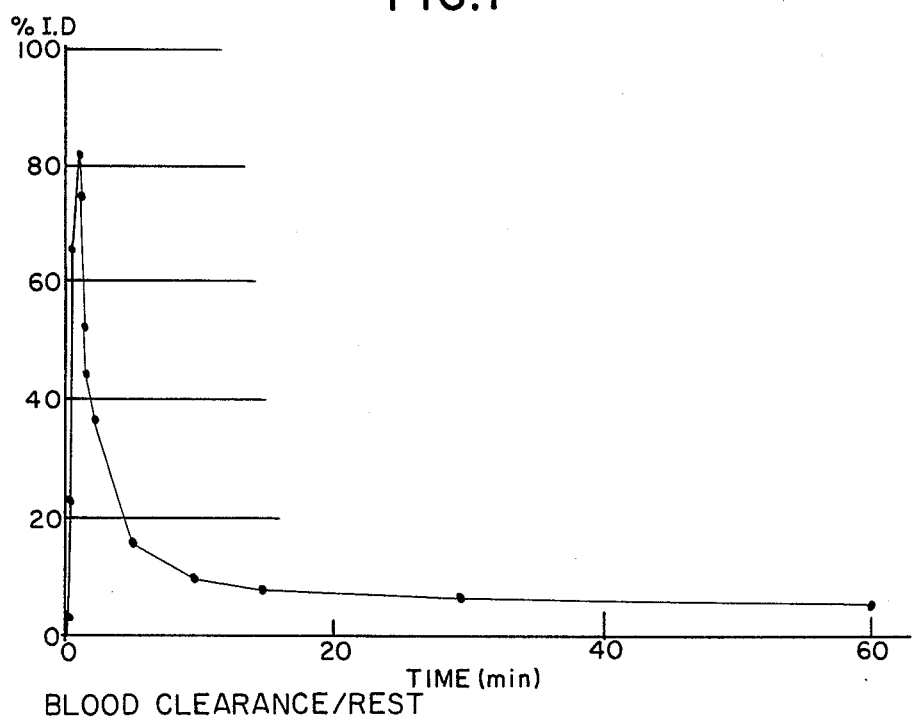
FIG. 2 is a graph showing blood clearance from a human volunteer at rest of a myocardial imaging agent made according to the present invention.

To demonstrate the effectiveness of the myocardial imaging agent formed using the method of Example 4 about 13 millicuries of $^{99m}$Tc activity was injected into a human volunteer under stress (having exercised until the volunteer's heart rate was approximately 80% of maximum predicted by the patient's age and physical condition). Blood samples were then taken immediately after injection and for intervals up to 60 minutes thereafter. The blood clearance data are shown in FIG. 1. Likewise the same test was conducted on a human volunteer at rest and the data are shown in FIG. 2.

This demonstrates extremely quick and effective blood clearance which enables obtaining a clear useful myocardial image as soon as 5–10 minutes after injection. In fact, due to the effective blood clearance as well as the high heart/liver ratio very clear myocardial images, including computer assisted tomographic images, were obtained of these volunteers, making this a commercially acceptable positive myocardial imaging agent.

All the $^{99m}$Tc(III) complexes described above are administered intravenously as radiopharmaceuticals in a radioactive dose of from 0.01 mCi/ml to 10 mCi/ml most preferably 2 mCi/ml–5mCi/ml. The administration dose for humans is usually in the range 10–30 mCi.

Imaging of the heart can be carried out by scanning techniques after waiting an appropriate period of time to permit blood clearance of the radiopharmaceutical. For example, time dependent scintiscans of the chest region of a patient can be used. A computer interfaced 16 crystal, Ohio Nuclear Spectrometer can be used for these scans. The complexes of the present invention can also be used in single photon emission computed tomography as described in Beyer et al, Diagnostic Nuclear Medicine, Volume 1, No. 2, page 10 (summer of 1984).

The present invention is particularly suitable for use in a kit preparation. The kit preparation would consist of two sterile, pyrogen free vials, the first vial containing an effective ligand having the structure shown in Formula 1 in combination with an effective reducing agent in this case the tin chloride. This would be a lyophilized composition. The second vial would contain a protected salt of the phosphine ligand shown in Formula 3. Typically, this would be the phosphine salt bonded to HCl, H$_2$SO$_4$, iron(II), copper(I) or zinc(II). The acid salts are preferred. The kit would be used by injecting the purified 99m-pertechnetate obtained from a molybdenum generator into the first vial. This is heated as per Example 3. Saline is added to the second vial to dissolve the protected ligand. This saline solution is then added to the first vial which is heated to effect conversion to Tc(III). The contents of the first vial can be directly injected into the patient without further purification.

The $^{99m}$Tc(III) complexes of the present invention provide a radiopharmaceutical uniquely adapted for use in myocardial imaging of humans. These radiopharmaceuticals neither hang up in the blood system nor the liver and yet bind to the heart for long periods of time ( 5h) to provide useful positive human heart images.

Accordingly having described our invention, we claim:

1. A kit for preparing a technetium 99m myocardial imaging agent, said kit comprising:

a first and second vial, said first vial containing a lyophilized pyrogen free sterile mixture of an effective reducing agent and a ligand having the following general formula:

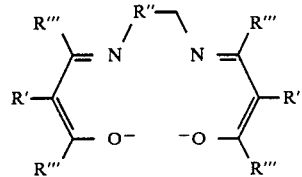

wherein R' and R''' represent H, hydroxyl, (C$_1$–C$_5$ alkyl, C$_1$–C$_5$ alkyl substituted by hydroxyl, ether, amide, ketone, aldehyde or nitrile groups and R'' represents C$_1$–C$_4$ alkylene, C$_1$–C$_4$ alkylene which may be substituted with hydroxyl, ether, amide, ketone, aldehyde or nitrile groups and wherein said second vial contains a lyophilized, pyrogen free, sterile protected salt of a phosphine ligand, said phosphine ligand having the following general formula:

wherein R$_4$ and R$_5$ represent the same or different group

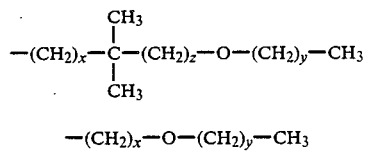

$-(CH_2)_x-O-(CH_2)_y-CH_3$ wherein X=1–4, Y=0–4 and Z=0–4 and wherein R$_3$ represents the same ligands represented by R$_4$ or R$_5$ or may represent: —OCH$_3$, —C$_1$–C$_5$ alkyl.

2. The kit claimed in claim 1 wherein said first ligand is H$_2$acac$_2$en.

3. The kit claimed in claim 1 wherein said effective reducing agent is tin chloride.

4. The kit claimed in claim 1 wherein said phosphine ligand comprises P(CH$_2$CH$_2$CH$_2$OCH$_3$)$_3$.

* * * * *

UNITED STATES PATENT AND TRADEMARK OFFICE
CERTIFICATE OF CORRECTION

PATENT NO. : 4,957,728
DATED : September 18, 1990
INVENTOR(S) : Deutsch et al.

It is certified that error appears in the above-indentified patent and that said Letters Patent is hereby corrected as shown below:

Please insert on the first page, column 1, immediately after the title, -- Research leading to the present invention was funded in part by the National Institute of Health, Grant No. AM-25252. Accordingly, the United States Government has certain rights in the invention. --

Signed and Sealed this

Twenty-second Day of November, 1994

*Attest:*

BRUCE LEHMAN

*Attesting Officer*    Commissioner of Patents and Trademarks